United States Patent [19]

Kotani et al.

[11] 4,008,141
[45] Feb. 15, 1977

[54] COMBINATION PH ELECTRODE

[75] Inventors: Haruo Kotani, Takatuki; Toshihiko Kunifusa; Kazunori Sasaki, both of Kyoto, all of Japan

[73] Assignee: Horiba, Ltd., Kyoto, Japan

[22] Filed: Aug. 29, 1975

[21] Appl. No.: 609,150

[30] Foreign Application Priority Data

Oct. 4, 1974   Japan ............................ 49-114970

[52] U.S. Cl. ........................ 204/195 G; 204/195 F
[51] Int. Cl.² ....................................... G01N 27/36
[58] Field of Search ....... 204/195 G, 195 F, 195 M

[56] References Cited
UNITED STATES PATENTS

| | | | |
|---|---|---|---|
| 2,755,243 | 7/1956 | Beckman et al. | 204/195 G |
| 3,399,667 | 9/1968 | Nishimoto et al. | 204/195 G |
| 3,434,953 | 3/1969 | Porter et al. | 204/195 G |
| 3,476,672 | 11/1969 | Snyder et al. | 204/195 G |
| 3,598,712 | 8/1971 | Petersen | 204/195 G |
| 3,694,338 | 9/1972 | Weingarten | 204/195 F |
| 3,700,577 | 10/1972 | Grauer | 204/195 F |
| 3,806,440 | 4/1974 | Gray et al. | 204/195 G |
| 3,879,279 | 4/1975 | Baucke | 204/195 G |

FOREIGN PATENTS OR APPLICATIONS 1,039,260   9/1958   Germany ..................... 204/195 G Primary Examiner—T. Tung
Attorney, Agent, or Firm—Wenderoth, Lind & Ponack

[57] ABSTRACT

A combination pH glass electrode and reference electrode assembly wherein the glass electrode can be easily detached for replacement.

1 Claim, 9 Drawing Figures

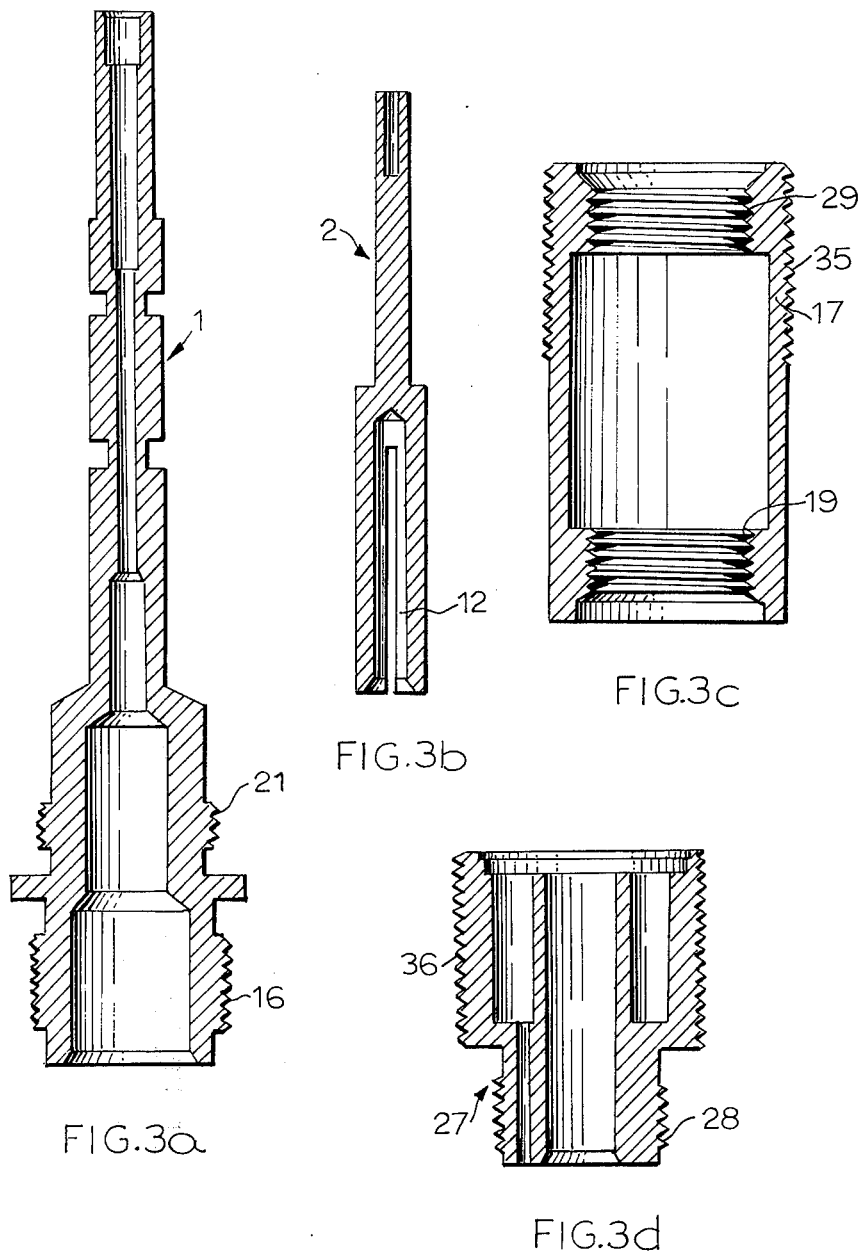

COMBINATION PH ELECTRODE

BACKGROUND OF THE INVENTION

The present invention relates to a combination electrode for the measurement of PH. For the measurement of PH by the method of electrode potential, since it is necessary to use a glass electrode and a reference electrode, a combination electrode which is a combination of the said two electrodes into a body has been widely used. In this case, a glass membrane which is the most important part of the electrode, is delicate and easily damaged and accordingly, it is necessary to change or replace it very often. Since the said combination electrode is a combination of two electrodes, a glass electrode and a reference electrode, into a single body, when the glass membrane is damaged or abraded and becomes impossible to use further, it is necessary to exchange the whole combination electrode itself. This is a serious disadvantage of the said combination electrode. In order to overcome such a disadvantage, devices have been proposed, for example, such as disclosed in Japanese Utility Model Application published as 19657/1967, wherein the outside tube has the specific shape of the letter Y, which is very inconvenient for use or for storage. Moreover, in the cited Japanese Utility Model Application, when the glass membrane is damaged, even if it is possible to exchange the glass electrode, it is also necessary to change the out-side lead wire to be connected to a detector (a voltmeter), since the lead wire is attached to the glass electrode in a unitary body.

SUMMARY OF THE INVENTION

The present invention provides a combination electrode, in which when the glass membrane, which is the important element in the combination electrode and is very delicate and is damaged easily and accordingly is necessary to change very often, must be changed due to abrasion or damage thereof, the part which is changed is small and the change can be carried out easily and moreover the amount of materials discarded is very small.

Furthermore, the present invention provides a combination electrode in which the out-side protection is strong and is not destroyed by a simple impact or blow in which the body has a smart rod-like shape and accordingly, is very easy to handle during the use or storage of the electrode.

BRIEF DESCRIPTION OF THE DRAWINGS

The attached drawings show one embodiment of the present invention, wherein:

FIGS. 3a-3f are sectional elevational views of parts thereof; and

DETAILED DESCRIPTION OF THE PREFERRED EMBODIMENT

Figure 1:
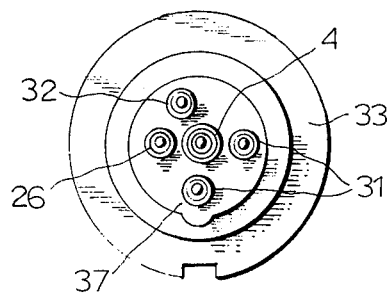
FIG. 1 is an end view of the combination electrode of the invention.
Figure 2:
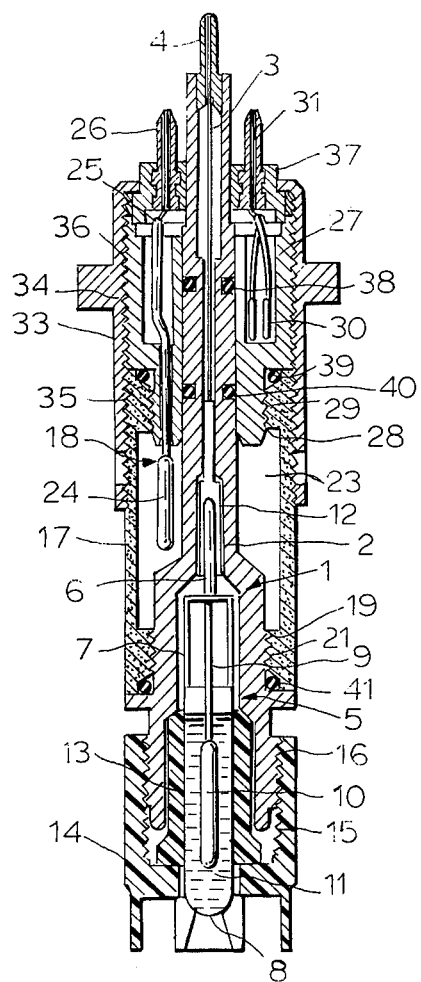
FIG. 2 is a longitudinal section thereof.
Figure 3E:
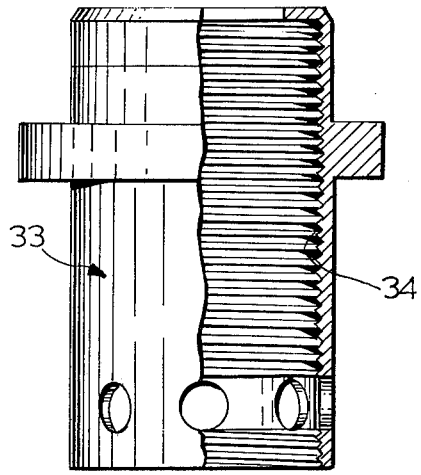
Figure 3F:
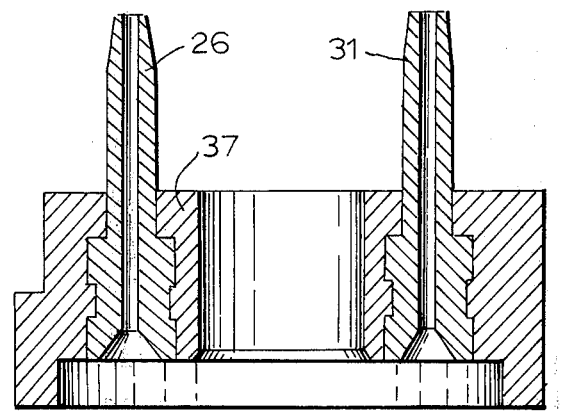
Figure 4:
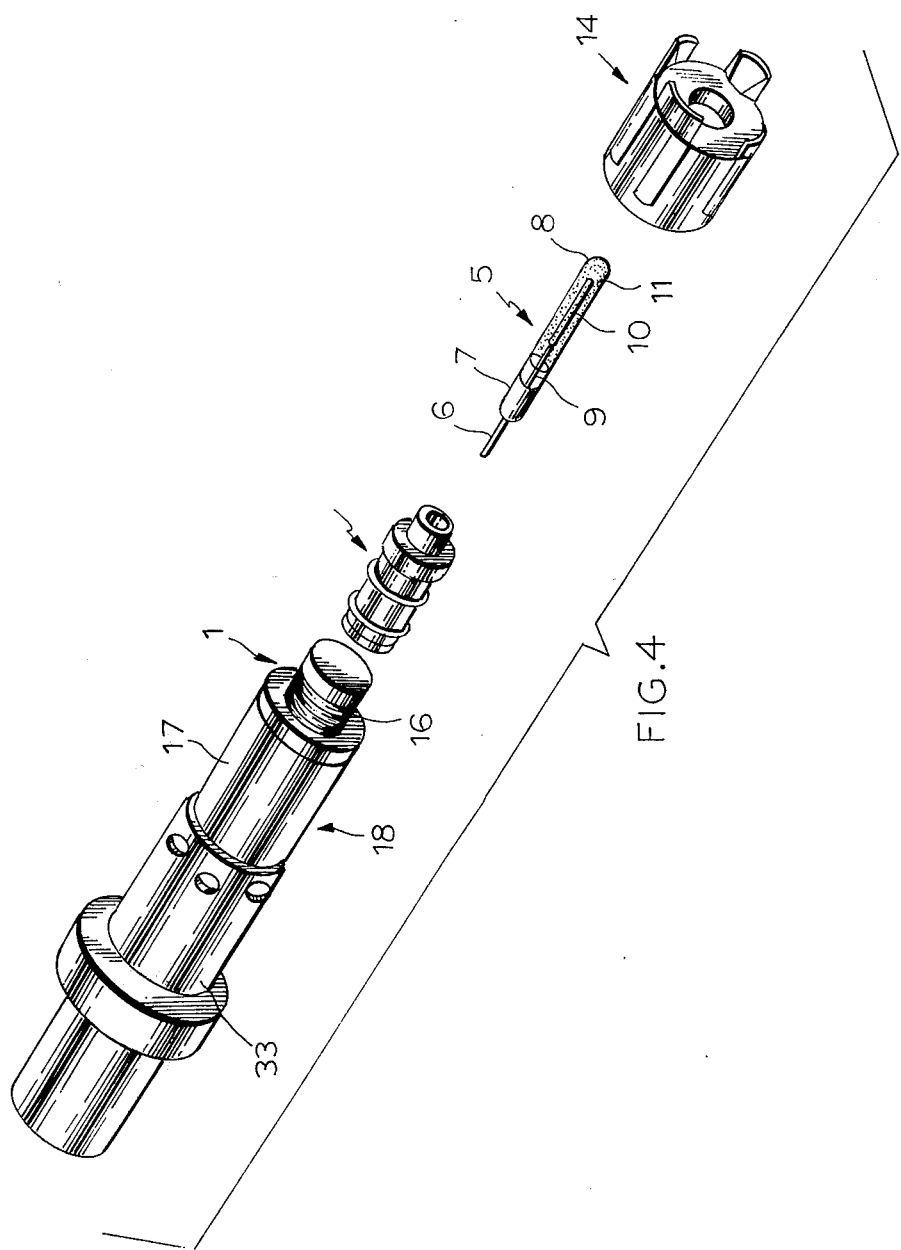
FIG. 4 is an exploded perspective view of the combination electrode.

Referring to the drawings, a central hollow body 1 having a cylindrical shape has a contact pin 2 therein which can be easily inserted into the inside of the central body 1 or can be easily removed therefrom and which is electrically connected with a detector, such as a voltmeter (not shown) through a lead wire 3 and a lead pin 4. A glass electrode provided with necessary but minimum number of parts such as a cap part 7 which has a protruding lead pin 6, a glass membrane 8, an internal lead wire 9, an internal electrode 10 and an internal solution 11 (for example, a saturated aqueous solution of potassium chloride). The glass electrode 5 is constructed so as to be easily inserted into the inside of the central body 1 from the open bottom end thereof and, of course, easily removed therefrom, if necessary. The lead pin 6 fits tightly into a concave portion 12 of the contact pin 2. A packing 13 coated with hydrophobic material such as polytetrafluoroethylene resin can be inserted easily into the space between the glass electrode 5 and the central body 1 to prevent the invasion of a sample solution into the inside of the central body 1 and, of course, can easily be taken out. A protecting cap 14 of plastic material for the protection of the glass electrode is threaded by threads 15 onto threads 16 on the outside of the central body 1 of said glass electrode 5 and, of course, the protection cap can be easily placed on or taken off. The glass electrode 5 is fixed in the combination electrode by the central body 1, the packing 13 and the cap 14. A side wall 17 of a strong and porous material such as organic material examples of which are polypropylene, polyethylene, polyvinyl chloride and Teflon, etc. or inorganic ceramic material the main component of which is metallic oxide, for example, $Al_2O_3$ or $SiO_2$, or inorganic ceramic material coated with an organic material, etc. and the side wall 17 forms a liquid junction of a reference electrode 18. Furthermore, the side wall 17 is threaded onto the central body 1, by screw threads 19 and 21 and, of course side wall 17 can be placed on or taken off central body 1 easily. An internal solution (for example, a saturated aqueous solution of potassium chloride) for the reference electrode is provided in space 23 and an internal electrode 24 extends into space 23 and is connected with a lead pin 26 through a lead wire 25. A second body 27 is threaded by threads 28 into threads 29 on the inside wall of the upper part of the said side wall 17. A thermister provided in the said second body 27 and is used for calibration of temperature. A lead pin 31 is connected with the thermistor 30, a lead pin 32 is provided for connection to ground and a metallic cap 33 is threaded by threads 34 into threads 35 on side wall 17 and threads 36 on the second body 27. For supplying the internal solution 23 or added to it, the metallic cap 33 and the second body 27 are taken off. As shown in FIG. 2, the combination electrode of the present invention has the upper part protected by the said metallic cap 33, the middle part protected by the side wall 17 and the lower part protected by the said protection cap 14, respectively. Further, a pin housing 37 is provided at the top of the second body 27 and O-rings 38-41 are provided between the various parts to prevent leakage of the internal solution from space 23.

From the foregoing description, it can be understood that to exchange the glass membrane 8, which is most important and so delicate as to be damaged more easily than the other various parts of the combination electrode, the exchange can be easily carried out by taking out the glass electrode 5 after the simple preparatory steps of taking off the protection cap 14 and the packing 13.

Furthermore, since the glass electrode 5 of the present invention is constituted into a unit which has as small a number of necessary parts as possible for a glass electrode, such as the cap 7 which has the protruding lead pin 6, the glass membrane 8, the internal lead wire 9, the internal electrode 10 and the internal solution 11, etc., the number of parts and amount of materials which are disposed of for every change are small and accordingly, the combination electrode of the present invention is economical.

Furthermore, since the combination electrode of the present invention is protected by the metallic cap 33 at the top, by the strong side wall 17 in the middle part and by the protection cap 14 at the bottom, the electrode can not be damaged by a simple collision with another body and moreover, the body of the combination electrode of the present invention, as a whole, can have a compact shape, for example, a rod-like shape as shown in FIG. 2, since the glass electrode 5 is inserted into the inside of the central body 1 and the reference electrode 18 is fitted to the outside of the central body 1, and this makes for ease in handling, use and storage.

What is claimed is:

1. A combination electrode for measuring pH values, comprising; a central body having a glass electrode receiving recess therein with a contact pin having a lead pin receiving recess therein at the internal end of said glass electrode receiving recess; a glass electrode having a glass membrane, an internal electrode in said glass membrane, a cap and a lead pin thereon with an internal lead extending from said internal electrode to said lead pin, said glass electrode being removably fitted into said glass electrode receiving recess with said lead pin in said lead pin receiving recess, the glass membrane projecting beyond the end of said central body; a protecting cap removably mounted on said central body around said glass electrode and having a lower open end projecting beyond the end of the glass membrane for protecting the glass electrode in the glass electrode receiving recess; a packing around said glass electrode in said glass electrode receiving recess and engaged by said protecting cap for being held in position in said recess; a second body mounted on said central body, a porous side wall removably mounted on said bodies and defining with said bodies an internal solution receiving space, an internal electrode removably mounted in said internal solution receiving space and having a lead and a lead pin extending out of the end of the combination electrode remote from said protecting cap, a thermistor removably mounted in said second body and having leads and lead pins extending out of the end of said combination electrode remote from said protecting cap, a further lead pin connected to said contact pin in said central body also extending out of the end of the combination electrode remote from said protecting cap, and a second protecting cap removably mounted around the outside of said second body.

* * * * *